US007504337B2

(12) United States Patent
Barton et al.

(10) Patent No.: US 7,504,337 B2
(45) Date of Patent: Mar. 17, 2009

(54) IC CHIP UNIFORM DELAYERING METHODS

(75) Inventors: Keith E. Barton, Hyde Park, NY (US); Thomas A. Bauer, Poughkeepsie, NY (US); Stanley J. Klepeis, Poughkeepsie, NY (US); John A. Miller, Wallkill, NY (US); Yun-Yu Wang, Poughquag, NY (US)

(73) Assignee: International Business Machines Corporation, Armonk, NY (US)

( * ) Notice: Subject to any disclaimer, the term of this patent is extended or adjusted under 35 U.S.C. 154(b) by 159 days.

(21) Appl. No.: 11/690,432

(22) Filed: Mar. 23, 2007

(65) Prior Publication Data

US 2008/0233751 A1 Sep. 25, 2008

(51) Int. Cl.
*H01L 21/461* (2006.01)
*H01L 21/302* (2006.01)

(52) U.S. Cl. ........................ 438/690; 438/691; 438/692; 438/693

(58) Field of Classification Search ........................ None
See application file for complete search history.

(56) References Cited

U.S. PATENT DOCUMENTS

| | | | |
|---|---|---|---|
| 5,718,618 A | | 2/1998 | Guckel et al. |
| 5,825,035 A | * | 10/1998 | Mizumura et al. ...... 250/423 R |
| 6,069,079 A | * | 5/2000 | Li .............................. 438/690 |
| 6,180,525 B1 | | 1/2001 | Morgan |
| 6,242,351 B1 | | 6/2001 | Li et al. |
| 6,258,721 B1 | | 7/2001 | Li et al. |
| 6,548,408 B1 | | 4/2003 | Morgan |
| 6,910,952 B2 | | 6/2005 | Suenaga et al. |
| 6,927,174 B2 | * | 8/2005 | Anciso et al. ............... 438/712 |
| 7,086,935 B2 | | 8/2006 | Wang |
| 7,090,564 B2 | | 8/2006 | Suzuki et al. |
| 2005/0060681 A1 | * | 3/2005 | Robson et al. ................. 716/21 |

FOREIGN PATENT DOCUMENTS

JP  2001085373 A  3/2001

* cited by examiner

*Primary Examiner*—Duy-Vu N Deo
(74) *Attorney, Agent, or Firm*—Lisa Jaklitsch; Hoffman Warnick LLC

(57) ABSTRACT

Methods of uniformly delayering an IC chip are disclosed. One embodiment includes: performing an ash on the wafer including an Al layer thereof and etching the Al layer; polishing an edge of the wafer using a slurry including an approximately 30 μm polishing particles; removing the aluminum layer and at least one metal layer by polishing using a slurry including approximately 9 μm diamond polishing particles and a non-abrasive backside of a polishing sheet; removing any remaining metal layers to a first metal layer by polishing using a slurry including approximately 3 μm diamond polishing particles and the non-abrasive backside of a polishing sheet; removing any scratches by polishing using a slurry including approximately 1 μm diamond polishing particles and the non-abrasive backside of a polishing sheet; and removing the first metal layer to a polyconductor layer by polishing using a colloidal slurry including approximately 0.25 μm diamond polishing particles.

7 Claims, 3 Drawing Sheets

IC CHIP UNIFORM DELAYERING METHODS

BACKGROUND

1. Technical Field

The disclosure relates generally to integrated circuit (IC) chip fabrication, and more particularly, to methods of uniformly delayering an IC chip for electron holography analysis.

2. Background Art

During IC chip fabrication, chips are periodically delayered so that structures therein can be evaluated. One technique used to evaluate the structures is electron beam holography, which allows evaluations of junction profiles. Precision and uniform delayering is important for electron holography analysis of an IC chip. In order to obtain uniform delayering, specific methods have to be used. One challenge to uniform delayering, among others, are copper pads within the IC chip. These copper pads prevent material from being adequately polished during delayering, and hence, create non-uniform delayering. One approach to this problem is to repetitively use a chemical etching method and reactive ion etching (RIE) in combination with polishing for each layer. This approach, however, takes a relatively extensive amount of time, e.g., 2-3 days. Another approach is to use a colloidal polishing slurry to remove layers. However, this approach causes non-uniformity delayering problems on the copper pads, i.e., colloidal polishing slurry does not work very well on copper. If several copper layers are present, the end results of colloidal polishing are the copper pad of top metal layers remains while the surrounding area of metal is totally removed. If a structure near the copper pad needs to be examined, the colloidal delayering may result in a very small useable area, such as 10 to 100 nm scale. The requirements for electron holography, however, is about 10-20 µm scale. In addition, because the particle size of the colloidal is relative small (approximately 0.05 µm size), polishing by colloidal is also very time consuming.

SUMMARY

Methods of uniformly delayering an IC chip are disclosed. One embodiment includes: performing an ash on the wafer including an Al layer thereof and etching the Al layer; polishing an edge of the wafer using a slurry including an approximately 30 µm polishing particles; removing the aluminum layer and at least one metal layer by polishing using a slurry including approximately 9 µm diamond polishing particles and a non-abrasive backside of a polishing sheet; removing any remaining metal layers to a first metal layer by polishing using a slurry including approximately 3 µm diamond polishing particles and the non-abrasive backside of a polishing sheet; removing any scratches by polishing using a slurry including approximately 1 µm diamond polishing particles and the non-abrasive backside of a polishing sheet; and removing the first metal layer to a polyconductor layer by polishing using a colloidal slurry including approximately 0.25 µm diamond polishing particles.

A first aspect of the disclosure provides a method of delayering an integrated circuit (IC) chip on a wafer, the method comprising: performing an ash on the wafer including an aluminum (Al) layer thereof and etching the aluminum (Al) layer; polishing an edge of the wafer using a slurry including an approximately 30 micrometer (µm) polishing particles; first removing the aluminum (Al) layer and at least one metal layer by polishing using a slurry including approximately 9 µm diamond polishing particles and a non-abrasive backside of a polishing sheet; second removing any remaining metal layers to a first metal layer by polishing using a slurry including approximately 3 µm diamond polishing particles and the non-abrasive backside of a polishing sheet; third removing any scratches by polishing using a slurry including approximately 1 µm diamond polishing particles and the non-abrasive backside of a polishing sheet; and fourth removing the first metal layer to a polyconductor layer by polishing using a colloidal slurry including approximately 0.25 µm diamond polishing particles.

A second aspect of the disclosure provides a method of delayering an integrated circuit (IC) chip on a wafer, the method comprising: performing an ash on the wafer including an aluminum (Al) layer thereof and etching the aluminum (Al) layer; polishing an edge of the wafer using a slurry including an approximately 30 micrometer (µm) polishing particles; first removing the aluminum (Al) layer and at least one metal layer by polishing using a slurry including approximately 9 µm diamond polishing particles and a non-abrasive backside of a polishing sheet; second removing any remaining metal layers to a first metal layer by polishing using a slurry including approximately 3 µm diamond polishing particles and the non-abrasive backside of a polishing sheet; third removing any scratches by polishing using a slurry including approximately 1 µm diamond polishing particles and the non-abrasive backside of a polishing sheet; and fourth removing the first metal layer to a polyconductor layer, including a silicide on the polyconductor layer, by polishing using a colloidal slurry including approximately 0.25 µm diamond polishing particles.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

Figure 1:
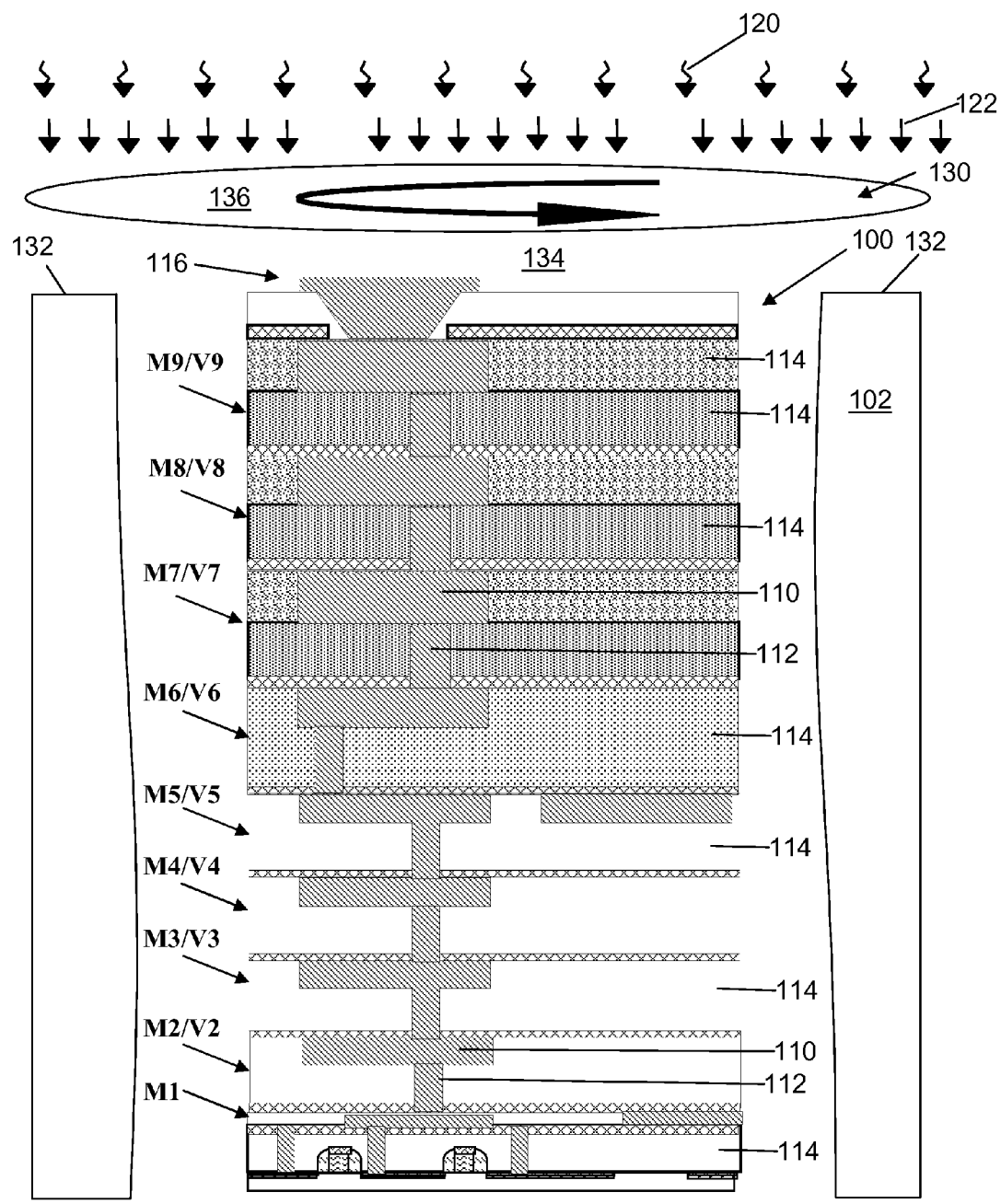
FIGS. 1-4 show cross-sectional views of an integrated circuit (IC) chip as it proceeds through embodiments of a method of delayering.

Referring to FIGS. 1-4, embodiments of a method of delayering an integrated circuit (IC) chip 100 on a wafer 102 are shown. FIG. 1 shows IC chip 100 including nine layers, M9/V9 down to first metal layer M1. It is understood that IC chip 100 may include a different number of layers, e.g., 10, 8, 7, 6, etc. Each layer M9/V9 to M2/V2 includes metal portions 110 and vias 112 positioned within a dielectric 114 (only some of each labeled). Dielectrics 114 may vary from layer to layer, and within a layer. For example, dielectrics 114 may include but are not limited to: silicon nitride ($Si_3N_4$), silicon oxide ($SiO_2$), fluorinated $SiO_2$ (FSG), hydrogenated silicon oxycarbide (SiCOH), porous SiCOH, boro-phospho-silicate glass (BPSG), etc. Metal portions 110 and vias 112 may include conductive material, e.g., metals such as copper, tungsten, titanium, etc., and appropriate liners (not shown). An aluminum layer 116 provides an uppermost layer of IC chip 100 and wafer 102. IC chip 100 may be formed using any now known or later developed techniques.

FIG. 1 also shows a first process including performing an ash 120 on wafer 102 including aluminum (Al) layer 116 thereof and (partially) etching 122 aluminum (Al) layer 116, e.g., a reactive ion etch (RIE). Ash 120 includes etching using an oxygen-containing plasma. FIG. 1 also shows polishing 130 an edge 132 (FIG. 1 only) of wafer 102 using a slurry 134 including an approximately 30 micrometer (μm) polishing particles. The polishing particles may include, for example, colloidal, 0.05 μm. As used herein, "slurry" includes a liquid including a suspended abrasive, e.g., silica, diamond, etc., and "polishing" is a process applied to either reduce roughness of the wafer surface as part of a delayering process or to remove excess material from a surface (i.e., delayer). Polishing includes a mechanical-chemical process using a rotating mechanical polishing pad (e.g., pad 136 in FIG. 1) and a slurry.

Figure 2:
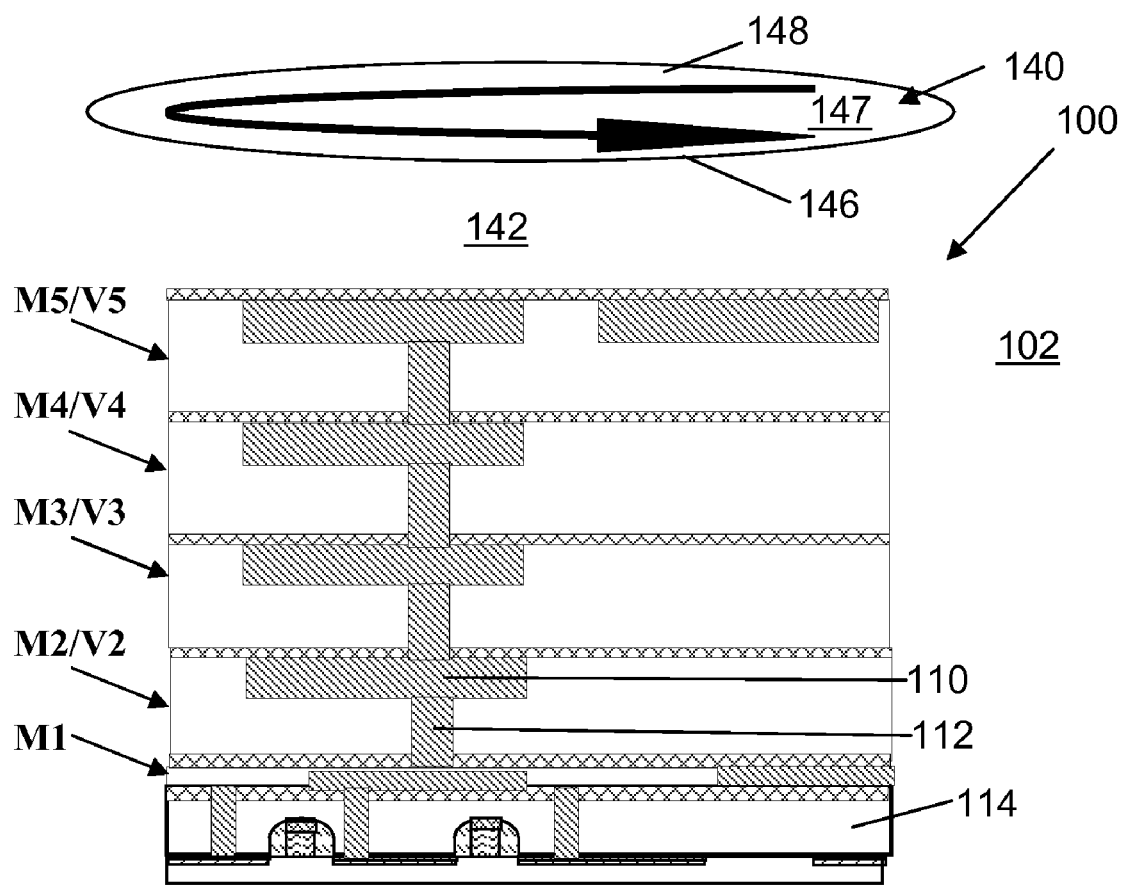

Turning to FIG. 2, another process includes removing aluminum (Al) layer 116 (FIG. 1) and at least one metal layer, e.g., at least one of M9/V9 to M2/V2 (up to M5/V5 shown), by polishing 140 using a slurry 142 including approximately 9 μm diamond polishing particles and a non-abrasive backside 146 of a polishing sheet 148. Non-abrasive backside 146 is typically of a plastic material that does not include abrasives, which are typically used on a front side 147 of a polishing sheet 148. Example polishing sheets used are available from Fujimi and Allied, model number 180-1005 Final APSA Back Polish Pad. For example, a 661×3M imperial diamond lapping film with 3 mil backing may be used.

Figure 3:
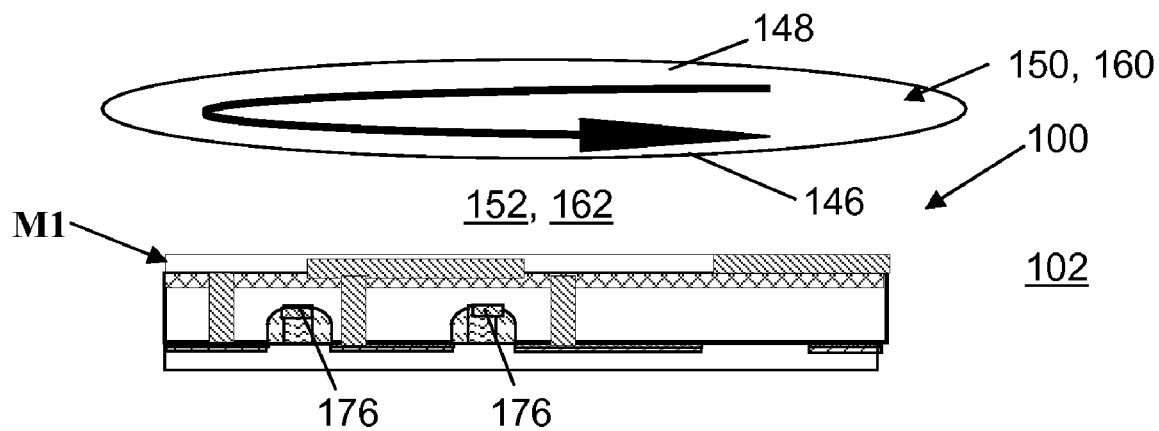

FIG. 3 shows removing any remaining metal layers M5/V5 to M2/V2 to a first metal layer M1 by polishing 150 using a slurry 152 including approximately 3 μm diamond polishing particles and non-abrasive backside 146 of polishing sheet 148. FIG. 3 also shows removing any scratches by polishing 160 using a slurry 162 including approximately 1 μm diamond polishing particles and non-abrasive backside 146 of polishing sheet 148.

Figure 4:
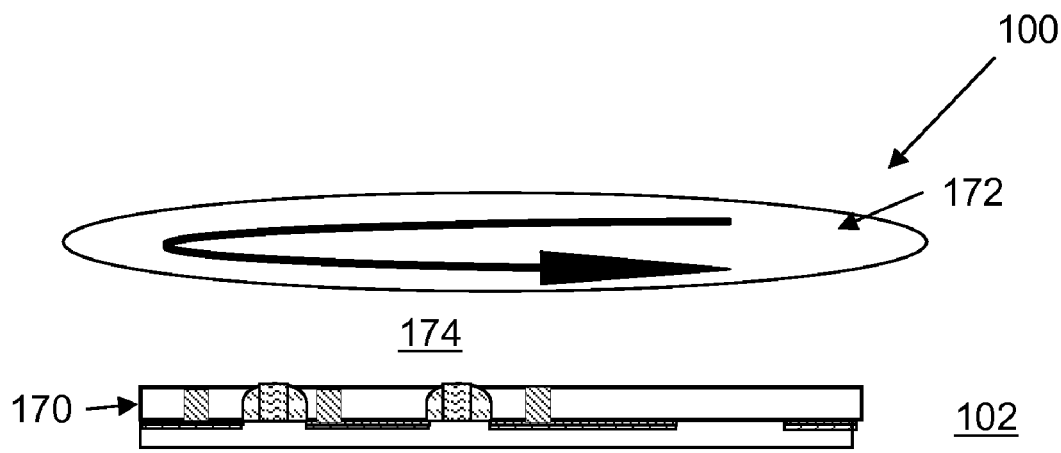

FIG. 4 shows removing first metal layer M1 (FIG. 3) to a polyconductor layer 170 by polishing 172 using a colloidal slurry 174 including approximately 0.25 μm diamond polishing particles. A "colloidal slurry" may include a type of slurry with polishing particles in a state intermediate between a homogeneous mixture (i.e., a solution) and a heterogeneous mixture. Colloidal slurry 174 may include, for example, silica polishing particles along with the diamond. Polishing 172 also removes a silicide 176 (FIG. 3) from polyconductor layer 170. Silicide 176 (FIG. 3) may include any now known or later developed silicon metal alloy, including such metals as, e.g., titanium, nickel, cobalt, etc. In one embodiment, polishing 172 occurs at approximately 120 revolutions per minute (rpm).

During the above-described embodiments, a colloidal silica may be intermittently applied to, for example, lubricate and assist polishing. However, this is not always necessary.

In contrast to conventional delayering techniques, the above-described embodiments may take as little as approximately one to two hours. In addition, uniform delayering to the poly-gate region with 100-500 μm area near the region of copper pads from more than 10 metal levels up is possible.

The methods as described above are used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The foregoing description of various aspects of the disclosure has been presented for purposes of illustration and description. It is not intended to be exhaustive or to limit the disclosure to the precise form disclosed, and obviously, many modifications and variations are possible. Such modifications and variations that may be apparent to a person skilled in the art are intended to be included within the scope of the disclosure as defined by the accompanying claims. Furthermore, the numerical denotations, i.e., first, second, third, fourth, in the claims is not meant to denote any order.

What is claimed is:

1. A method of uniformly delayering an integrated circuit (IC) chip on a wafer, the method comprising:
    performing an ash on the wafer including an aluminum (Al) layer thereof and etching the aluminum (Al) layer;
    polishing an edge of the wafer using a slurry including an approximately 30 micrometer (μm) polishing particles;
    first removing the aluminum (Al) layer and at least one metal layer by polishing using a slurry including approximately 9 μm diamond polishing particles and a non-abrasive backside of a polishing sheet;
    second removing any remaining metal layers to a first metal layer by polishing using a slurry including approximately 3 μm diamond polishing particles and the non-abrasive backside of a polishing sheet;
    third removing any scratches by polishing using a slurry including approximately 1 μm diamond polishing particles and the non-abrasive backside of a polishing sheet; and
    fourth removing the first metal layer to a polyconductor layer by polishing using a colloidal slurry including approximately 0.25 μm diamond polishing particles.

2. The method of claim 1, wherein the fourth removing further includes removing a silicide from the polyconductor layer.

3. The method of claim 1, wherein the fourth removing includes polishing at approximately 120 revolutions per minute (rpm).

4. The method of claim 1, further comprising intermittently applying a colloidal silica.

5. A method of uniformly delayering an integrated circuit (IC) chip on a wafer, the method comprising:
    performing an ash on the wafer including an aluminum (Al) layer thereof and etching the aluminum (Al) layer;
    polishing an edge of the wafer using a slurry including an approximately 30 micrometer (μm) polishing particles;
    first removing the aluminum (Al) layer and at least one metal layer by polishing using a slurry including approximately 9 μm diamond polishing particles and a non-abrasive backside of a polishing sheet;
    second removing any remaining metal layers to a first metal layer by polishing using a slurry including approximately 3 μm diamond polishing particles and the non-abrasive backside of a polishing sheet;

third removing any scratches by polishing using a slurry including approximately 1 µm diamond polishing particles and the non-abrasive backside of a polishing sheet; and fourth removing the first metal layer to a polyconductor layer, including a silicide on the polyconductor layer, by polishing using a colloidal slurry including approximately 0.25 µm diamond polishing particles.

6. The method of claim 1, wherein the fourth removing includes polishing at approximately 120 revolutions per minute (rpm).

7. The method of claim 1, further comprising intermittently applying a colloidal silica.

* * * * *